United States Patent
Dagher et al.

(10) Patent No.: US 9,165,353 B2
(45) Date of Patent: Oct. 20, 2015

(54) SYSTEM AND METHOD FOR JOINT DEGRADATION ESTIMATION AND IMAGE RECONSTRUCTION IN MAGNETIC RESONANCE IMAGING

(75) Inventors: Joseph Dagher, Tucson, AZ (US); Francois Georges Meyer, Louisville, CO (US)

(73) Assignee: THE GENERAL HOSPTIAL CORPORATION, Boston, MA (US)

( * ) Notice: Subject to any disclaimer, the term of this patent is extended or adjusted under 35 U.S.C. 154(b) by 46 days.

(21) Appl. No.: 14/241,494

(22) PCT Filed: Aug. 31, 2012

(86) PCT No.: PCT/US2012/053384
§ 371 (c)(1),
(2), (4) Date: Jul. 10, 2014

(87) PCT Pub. No.: WO2013/033558
PCT Pub. Date: Mar. 7, 2013

(65) Prior Publication Data
US 2014/0314293 A1    Oct. 23, 2014

Related U.S. Application Data

(60) Provisional application No. 61/530,264, filed on Sep. 1, 2011.

(51) Int. Cl.
G06K 9/00 (2006.01)
G06T 5/50 (2006.01)
A61B 5/055 (2006.01)
G01R 33/565 (2006.01)
A61B 5/00 (2006.01)
G06T 5/00 (2006.01)

(52) U.S. Cl.
CPC . *G06T 5/50* (2013.01); *A61B 5/055* (2013.01); *A61B 5/7203* (2013.01); *G01R 33/565* (2013.01); *G06T 5/001* (2013.01); *G01R 33/56527* (2013.01); *G01R 33/56536* (2013.01); *G01R 33/56563* (2013.01); *G06T 2207/10088* (2013.01)

(58) Field of Classification Search
None
See application file for complete search history.

(56) References Cited

U.S. PATENT DOCUMENTS

| | | | |
|---|---|---|---|
| 6,134,464 A * | 10/2000 | Tan et al. | 600/410 |
| 6,259,250 B1 | 7/2001 | Mock | |
| 6,341,179 B1 | 1/2002 | Stoyle et al. | |
| 6,795,723 B1 | 9/2004 | Liu | |

(Continued)

FOREIGN PATENT DOCUMENTS

RU    2423718 C2    7/2011

OTHER PUBLICATIONS

International Search Report and Written Opinion under date of mailing of Dec. 13, 2012 in connection with PCT/US2012/053384.

*Primary Examiner* — Atiba O Fitzpatrick
(74) *Attorney, Agent, or Firm* — Quarles & Brady, LLP

(57) ABSTRACT

A magnetic resonance imaging (MRT) method for jointly estimating an image degradation and reconstructing an image of a subject in which that image degradation is mitigated is provided. The MRI system is operated to acquire multiple different k-space data sets that are acquired with different acquisition parameters so as to modulate the image degradation to be estimated. Using an iterative process, the image degradation is estimated while jointly reconstructing an image in which the estimated image degradation is mitigated.

12 Claims, 3 Drawing Sheets

(56) References Cited

U.S. PATENT DOCUMENTS 7,230,424 B1 * 6/2007 Morrone ........................ 324/309
2002/0156364 A1 * 10/2002 Madore ......................... 600/410
2002/0190714 A1 * 12/2002 Bernstein ...................... 324/307
2007/0096732 A1 * 5/2007 Samsonov et al. ............ 324/309

* cited by examiner

SYSTEM AND METHOD FOR JOINT DEGRADATION ESTIMATION AND IMAGE RECONSTRUCTION IN MAGNETIC RESONANCE IMAGING

CROSS-REFERENCE TO RELATED APPLICATIONS

This application represents the national stage entry of PCT International Application No. PCT/US2012/053384 filed Aug. 31, 2012, which claims the benefit of U.S. Provisional Patent Application 61/530,264, filed on Sep. 1, 2011, the disclosures of which are hereby incorporated by reference in their entirety for all purposes.

STATEMENT REGARDING FEDERALLY SPONSORED RESEARCH

This invention was made with government support under MH015442 awarded by the National Institutes of Health. The government has certain rights in the invention.

BACKGROUND OF THE INVENTION

The field of the invention is systems and methods for magnetic resonance imaging ("MRI"). More particularly, the invention relates to systems and methods for jointly estimating image degradation and reconstructing images in which the image degradation is mitigated.

One of the main goals of MRI is to obtain an accurate representation of the object or to estimate underlying physiological quantities of interest. However, there are many factors that degrade (e.g., blur) the images obtained with an MRI system and, therefore, inhibit the image reconstruction or parameter estimation tasks. The sources of these degradations can be external or internal with respect to the imaged object. External sources of degradation, such as imperfections in the magnet or electronics, can be addressed by improved hardware designs. However, internal sources result in degradations that are more conspicuous and challenging to correct.

Physiologically induced internal sources are often times (directly or indirectly) related to the quantities to be estimated. For example, there are instances in which it is desired to estimate the various chemical content within a slice in the object of interest; however, this spatially varying chemical content induces a spatially varying resonance profile. Under rapid imaging conditions, this spatially varying resonance profile causes very serious artifacts including signals being completely shifted from their true position. This is but one example where the quantities to be estimated (chemical content) directly relate to the artifacts produced in the images. There are also many situations where the artifacts are indirectly related to the quantities that it is desired to estimate.

One such example is in the area of functional MRI, or fMRI. In this imaging application, the objective is to estimate signal levels due to neuronal activation in certain regions in the brain. Neuronal firing, however, is also correlated with increased blood volume, which in turn changes the local magnetic field in that region. These field inhomogeneities often cause signal loss, thereby confounding the task of interest. In general, such susceptibility-induced field inhomogeneities arises at tissue boundaries, such as between airbone interfaces (brain) and airtissue interfaces (brain, intestines, lungs). These inhomogeneities result in images with severe artifacts, including signal loss and geometric distortion or warping. Other examples of internal degradations include blood flow effects, which introduce motion artifacts completely overriding the signal of interest. In that context, estimating the speed of the blood (or the flow) becomes a daunting task, where the artifacts are a function of the parameters to be estimated.

The foregoing examples describe situations in which the degradations arise during the acquisition process. The challenge with these situations is that the degradations are often unknown; thus, it is unknown how to invert them. In addition, the degradations severely affect the measurements, thereby making it difficult to estimate the degradations from the data itself. All this in turn directly or indirectly inhibits the image reconstruction or parameter estimation task of interest.

In order to solve this class of problems, the traditional approach has been to either fine tune the acquisition parameters so that the obtained images are as "artifact-free" as possible, or to design post-processing methods that correct for those artifacts using some estimates or prior assumptions about the inherent degradations. These methods are either sub-optimal or impractical and, therefore, there remains a need to provide a method for reconstructing quality images in the presence of significant degradation sources.

SUMMARY OF THE INVENTION

The present invention overcomes the aforementioned drawbacks by providing a joint degradation estimation and image reconstruction method. Multiple, diverse data acquisitions are obtained from the same subject. Degradation parameters can be recovered while simultaneously reconstructing an image of the subject from the acquired data.

Thus, it is an aspect of the invention to provide a method for jointly estimating an image degradation and reconstructing an image of a subject using a magnetic resonance imaging ("MRI") system. The MRI system is used to acquire a k-space data set, and this process is repeated to acquire multiple k-space data sets while using a different acquisition parameter during each repetition such that each of the multiple k-space data sets is acquired using a different acquisition parameter. The image degradation is estimated jointly while reconstructing an image of the subject in which the image degradation is mitigated. This joint estimation reconstruction is performed iteratively and includes the steps of estimating the image degradation from the multiple k-space data sets and reconstructing the image of the subject in which the image degradation is mitigated using the estimated image degradation and the multiple k-space data sets.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
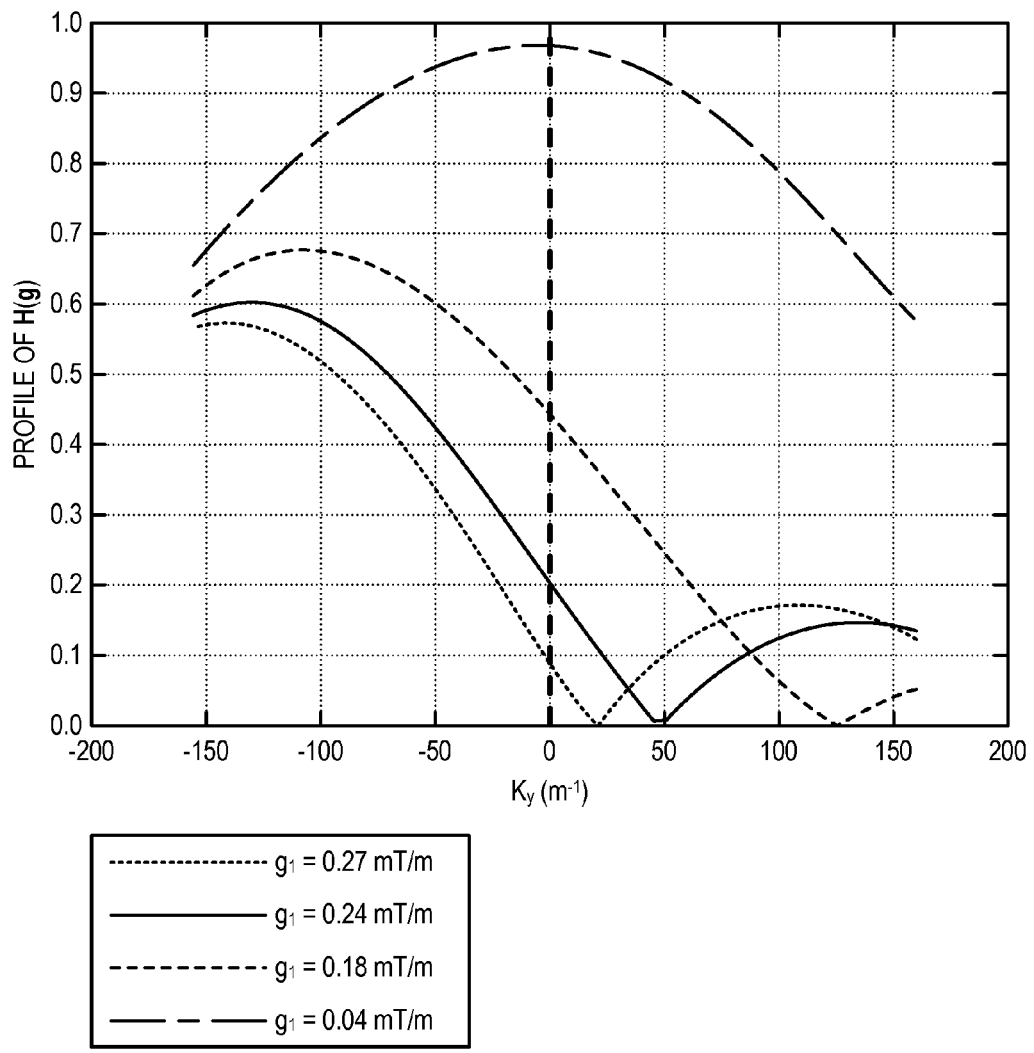
FIG. 1 is a plot of the profiles of different examples of forward model matrices for different values of shift-variant inhomogeneity coefficients, which are representative of the degradation parameters.

One of the main sources of signal degradation in rapid MR acquisitions, such as echo planar imaging ("EPI"), is magnetic field variations caused by field inhomogeneities and susceptibility gradients. If unaccounted for during the reconstruction process, this spatially-varying field can cause severe image artifacts. The present invention provides a solution to this problem by providing a method for joint acquisition processing. For instance, the present invention provides a multi-image acquisition strategy and a corresponding joint estimation reconstruction algorithm. The estimation step computes the spatial distribution of the magnetic field maps, while the reconstruction step yields, for example, a minimum mean squared error ("MMSE") estimate of the imaged slice. The method is robust and efficient, offering factors of improvement in the quality of the reconstructed image as compared to other traditional methods.

In a two-dimensional slice-selective imaging scan, the signal induced by an elemental volume, dV, in an MRI receiver coil is given by:

$$dS \propto f(x, y, z, t) \exp\left(i2\pi(xK_x(t) + yK_y(t)) + \gamma \int_0^t \Delta B(x, y, z, \tau) d\tau\right) dV; \quad (1)$$

where f(x,y,z,t) represents the spatiotemporal distribution of the object, $\gamma$ is the gyromagnetic ratio in Hz/T, and $K_x(t)$ and $K_y(t)$ denote the spatial frequencies encoded by the readout and phase-encoding gradients, respectively, at time, t. The term $\Delta B(x,y,z,t)$ represents the deviations from the desired magnetic field as controlled by the gradients. The sources of these inhomogeneities are either external (e.g., main field or magnetic field gradient inhomogeneities, gradient coil non-linearity), or due to internal differences between the magnetic susceptibility of different materials. The susceptibility-induced inhomogeneities can be very severe, particularly when they arise across air/tissue or air/bone interfaces. For example, in the brain, large susceptibility gradients occur around the anterior-frontal regions, temporal lobes, and around the sinuses. In the absence of $\Delta B(x,y,z,t)$, the evolution of the spatial frequencies, $K_x$ and $K_y$, with time defines the grid over which measurements are made, as can be seen from Eqn. (1).

In the simple case of a regular rectangular grid, the relationship between the induced signal, S, and the object, f, amounts to a simple Fourier transform operation. The inhomogeneities, $\Delta B$, however, perturb the effective trajectory of $K_x(t)$ and $K_y(t)$. If not accounted for during the reconstruction process, these inhomogeneities will result in severe image artifacts including geometric warping and signal loss. These image artifacts can have detrimental effects, especially in tasks that require geometric accuracy, such as registration of fMRI data to brain atlases for activity localization; neurosurgery and computer-assisted surgery; rigid-body segmentation; and so on. Ultimately, these artifacts influence the statistical decision about the presence or absence of neuronal activation. Since the inhomogeneity term, $\Delta B$, scales with magnetic field strength and long read-out time, the inhomogeneities and related artifacts get worse as the main magnetic field strength of MRI systems increases.

Traditional solutions to this problem can generally be divided into two classes: acquisition-based methods and processing-based methods. Acquisition-based methods modify the pulse sequence to carefully preempt inhomogeneities in specific regions via the careful calibration of gradients. This approach only partially corrects for the problem in one region, while increasing artifacts in other regions. Also, the additional pulse sequences often require an increase in the scan time, and place high demand on the shim coils. Processing-based algorithms attempt to reconstruct the object in two distinct steps. In the first step, an estimate of the field maps, $\Delta B(x,y,z)$, is computed either via a separate acquisition or from the distorted data itself. In the second step, the data is unwarped or de-blurred according to the field map estimate using post-processing methods. This approach often fails in instances of inhomogeneity-induced signal loss, as it becomes very difficult to estimate inhomogeneity and reconstruct data in regions overwhelmed by noise. Another drawback to these methods is that estimating the field maps from a separate scan is often inaccurate due to the estimate itself being warped and due to its dependence on subject motion and dynamic changes with physiological conditions.

Recently, a method that suggests the joint estimation and correction of distortion artifacts via a slight modification to EPI was proposed by H. Nguyen, et al., in "Joint Estimation and Correction of Geometric Distortions for EPI Functional MRI Using Harmonic Retrieval," *IEEE Transactions on Medical Imaging*, 2009; 3(28):423-434. However, similar to most processing-based techniques, the performance of this approach is inherently limited by signal losses. The present invention provides a more general technique that relies on the joint design of the acquisition method and corresponding reconstruction algorithm. Specifically, the method of the present invention includes modifying the data acquisition to acquire diverse sets of k-space data. The diversity of the measurements allows the reconstruction of an image, even in cases of severe signal loss.

The present invention provides a method for joint acquisition processing that can be generally described as follows. First, instead of acquiring only one image or view of the object, multiple images or multiple views of the same object are acquired. Each of these multi-acquisitions are different from the others, thus forming a diverse set of acquisitions. This introduced diversity is carefully chosen, as will be described below in detail.

Given these multiple acquisitions, the most likely degradation profile, or sets of degradation values, that could have given rise to the multiple measurements is sought. The known modulation between the images that was introduced by the diversity of the multiple acquisitions is used to extract the inherent degradation or parameter of interest. Using this estimate of the inherent degradation, and the multiple measurements, an image of the object is reconstructed or parameters of interest are extracted from the measurement data.

As will be described below in more detail, the acquisition step involves slightly changing the acquisition method by introducing a term that modulates the measurement as a function of the inherent degradation. This modulation term is carefully chosen as a function of the degradations that are to be estimated or extracted. The degradation estimation and image reconstruction steps involve a signal processing algorithm that is designed to jointly estimate the degradation parameters and reconstruct the image of the object.

An example of the method of the present invention is provided below with respect to estimating susceptibility-induced field variations in two-dimensional echo planar imaging ("EPI") and reconstructing the resulting degraded image. It will be appreciated by those skilled in the art, however, that this method can be readily extended to other applications with different pulse sequences and different degradations to be estimated.

By way of example, a forward model that describes the two-dimensional image formation process in echo planar imaging ("EPI") is provided. Starting from Eqn. (1), and using the discrete spatial frequency sampling of EPI:

$$K_x(t) = m\Delta k_x, \; -\frac{N_x}{2} \le m \le \frac{N_x}{2}; \tag{2}$$

$$K_y(t) = n\Delta k_y, \; -\frac{N_y}{2} \le n \le \frac{N_y}{2}; \tag{3}$$

the signal, $S(m\Delta k_x, n\Delta k_y)$, from the selected slice can be written as:

$$S = \int_{-\Delta Z/2}^{+\Delta Z/2} dz \tag{4}$$

$$\int\int f(x,y) \exp\{i2\pi(m\Delta k_x x + n\Delta k_y y + \gamma \Delta B(x,y,z)t)\} dx dy;$$

where $\Delta Z$ is the slice thickness and t is the sampling time for EPI. This sample time is given by:

$$t = TE + m\Delta t + nT$$

where TE is the echo time, t is the dwell time, and T is the time between two consecutive phase-encode lines, n. Going from Eqn. (1) to Eqn. (4), the object, f(x,y,z,t) has been approximated with f(x,y,z=0) and the $T_1$ and $T_2$ relaxation effects have been ignored. It has also been assumed that the inhomogeneities, $\Delta B$, are slowly varying compared to the data acquisition window. The spatial variation of the magnetic field, $\Delta B$, however, is more complicated and is determined by the underlying sources of inhomogeneities. As an example, the following model for the inhomogeneity term can be used:

$$\Delta B(x,y,z) \approx g_0(x,y) + g_1(x,y)z \tag{5}$$

where $\Delta B(x,y,z)$ has been expanded in z, and where $g_0(x, y)$ and $g_1(x, y)$ are the zeroth and first order shift-variant inhomogeneity coefficients ("SICs"), respectively. The model in Eqn. (5) takes into account both in-plane field inhomogeneities, $g_0(x,y)$, and susceptibility-induced field gradients across the slice-selective direction, $g_1(x,y)$, which in this example is along the z-direction.

The majority of existing inhomogeneity correction methods only consider one of these SIC terms at a time. Methods that focus on correcting $g_0$-related artifacts, such as pixel shift and region deformation, use signal processing methods to unwarp the images using estimates of $g_0(x,y)$ obtained via field maps. On the other hand, methods aiming to correct $g_1$-related signal losses, which could be very severe, generally use signal acquisition methods to recover the signal intensity in a localized region. The method of the present invention corrects for both artifacts using a joint acquisition-processing scheme. Replacing the $\Delta B$ term in Eqn. (4) with Eqn. (5) and integrating over z, the resulting discretized measurements can be written as:

$$S(m,n) = \iint f(x,y) \exp(i2\pi(m\Delta k_x x + n\Delta k_y y)) \cdot \exp(i2\pi$$
$$\gamma g_0(x,y)(TE+m\Delta t+nT)) \cdot \sin c(\pi \gamma \Delta z g_1(x,y)$$
$$(TE+m\Delta t+nT)) dx dy \tag{6}$$

Reconstructing f(x, y) from the discrete samples S(m,n) is a challenging task. In the method of the present invention, the reasonable assumption that there is interest in reconstructing $f(x_p, y_q)$ only on a discrete sampling grid, such as the one defined by the EPI sequence, can be made. Furthermore, it is assumed that the object and the SIC terms do not vary considerably inside any given pixel. It can be shown that this latter assumption allows Eqn. (6) to be rewritten as:

$$S(m,n) = \sum_{p=0}^{N_x-1} \sum_{q=0}^{N_y-1} f(x_p, y_q) \tag{7}$$

$$\exp\left(i2\pi\left(\frac{mp}{N_x} + \frac{nq}{N_y}\right)\right) \cdot \exp(i2\pi\gamma g_0(x_p, y_q)(TE+m\Delta t+nT))$$

$$\operatorname{sinc}\left(\frac{m}{N_x}\right) \cdot \operatorname{sinc}\left(\frac{n}{N_y}\right) \operatorname{sinc}(\pi\gamma\Delta z g_1(x_p, y_q)(TE+m\Delta t+nT));$$

where the additional sin c terms arise due to the grid of rectangular pixels and where $$x_p \Delta k_x = \frac{p}{N_x}; \tag{8}$$

and $$y_q \Delta k_y = \frac{q}{N_y}. \tag{9}$$

Equation (7) describes the forward model for two-dimensional EPI image formation, as corrupted by shift-variant inhomogeneities described in Eqn. (5). The transformation that maps the object, f, at locations $(x_p, y_q)$ into S at (m,n) is a four-dimensional matrix. This tensor relationship can be significantly simplified by observing that $\Delta t \ll T$, which implies that the SIC would have strong effects only along the y-direction. This fact is exploited in most EPI distortion correction techniques. Using some matrix manipulations, the $m^{th}$ row in Eqn. (7), $S_m$, can be written as:

$$S_m = \operatorname{sinc}\left(\frac{m}{N_x}\right) \sum_p \exp\left(i2\pi\left(\frac{mp}{N_x}\right)\right) \cdot s_{x_p}; \tag{10}$$

where $s_{x_p}$ is a $1 \times N_y$ vector given by:

$$s_{x_p} = f_p H_{x_p} \tag{11};$$

where $f_p$ is the $p^{th}$ row of the object. In Eqn. (11), $H_{x_p}$ is the $N_y \times N_y$ forward model matrix that maps the spatial index, $y_q$, to its conjugate index, n, for each $x_p$, and is given by:

$$H_{x_p}(y_q, n) = \exp\left(i2\pi\left(\frac{nq}{N_y}\right)\right) \exp(i2\pi\gamma g_0(x_p, y_q)(TE+nT)) \cdot \operatorname{sinc}\left(\frac{n}{N_y}\right) \tag{12}$$

$$\operatorname{sinc}(\pi\gamma\Delta z g_1(x_p, y_q)(TE+nT)).$$

Thus, the four-dimensional tensor forward model of Eqn. (7) has been transformed into N different two-dimensional forward model matrices. In doing so, the complexity of the model is reduced without sacrificing its accuracy.

To account for noise, the model in Eqn. (11) can be rewritten to include an additive noise term, $w_p$, $$m_p = f_p H_{x_p} + w_p \tag{13}.$$

From Eqn. (10), it can be seen that $s_{x_p}$ is the $p^{th}$ row of a matrix obtained by taking the inverse one-dimensional discrete Fourier transform ("DFT") across the rows of the matrix formed by stacking the row vectors as follows:

$$\frac{S_m}{\operatorname{sinc}\left(\frac{m}{N_x}\right)} \text{ for } m = 1, \ldots, N_x. \tag{14}$$

Thus, by solving Eqn. (11), the $p^{th}$ row of the object can be reconstructed from the vector $s_{x_p}$. Only a few methods in the literature attempt to correct for distortions using similar linear systems formulation. The lack in popularity of this approach is due to two obstacles. First, in the presence of noise, inverting $H_{x_p}$ in Eqn. (11) will yield highly unstable solutions. This is particularly true in regions with low signal, which is the case when the value of $g_1(x_p, y_q)$ is large. This difficulty can be addressed by separating $H_{x_p}$ into two matrices: one corresponding to $g_1(x_p, y_q)$ effects and the second including the remaining effects, as described by G. Liu and S. Ogawa in "EPI Image Reconstruction with Correction of Distortion and Signal Losses," *Journal of Magnetic Resonance Imaging*, 2006; 24(3):683-689. In the method taught by Liu and Ogawa, the matrix due to $g_1(x_p, y_q)$ is inverted using truncated iterative methods, thereby reducing the effects of noise amplification. Such a method is unable to fully reconstruct the signal in regions with large $g_1(x_p, y_q)$. The second obstacle with this approach is that $H_{x_p}$ and $f_p$ are both unknown. In their method, Liu and Ogawa make the common assumption that $g_0(x_p, y_q)$ and $g_1(x_p, y_q)$ do not change over the entire scan period; thus, their method uses a separate measurement at the beginning of the scan to get an estimate of these quantities. As described above, such an assumption is not realistic. This reconstruction problem can, therefore, be categorized in the class of parameterized blind signal deconvolution.

Standard methods used to estimate $H_x$ and $f_p$ become unreliable at low signal-to-noise ratios. As an example, FIG. 1 illustrates different profiles of $H_{x_p}$ at typical values of $g_1(x_p, y_q)$. It is noted that the value of the response is low around $K_y=0$, which implies that the corresponding measurement will be dominated by noise. In this instance, the processing-based techniques for estimating the forward model matrix, $H_{x_p}$, such as those described above, will be not be robust.

The present invention provides a joint acquisition-reconstruction method that overcomes the drawbacks of other methods by estimating the SIC or $H_{x_p}$ without using any prior knowledge and obtaining a linear minimum mean squared error ("LMMSE") reconstruction of the object, $f_p \forall p$. Hereafter, and for simplicity, only one matrix row is considered in the following description and the $x_p$ and $p$ indices are dropped from Eqn. (13).

In order to solve the problems presented above, a joint acquisition-processing method is provided. The method of the present invention does not require prior-knowledge of the field maps, $\Delta B(x,y)$.

Figure 2:
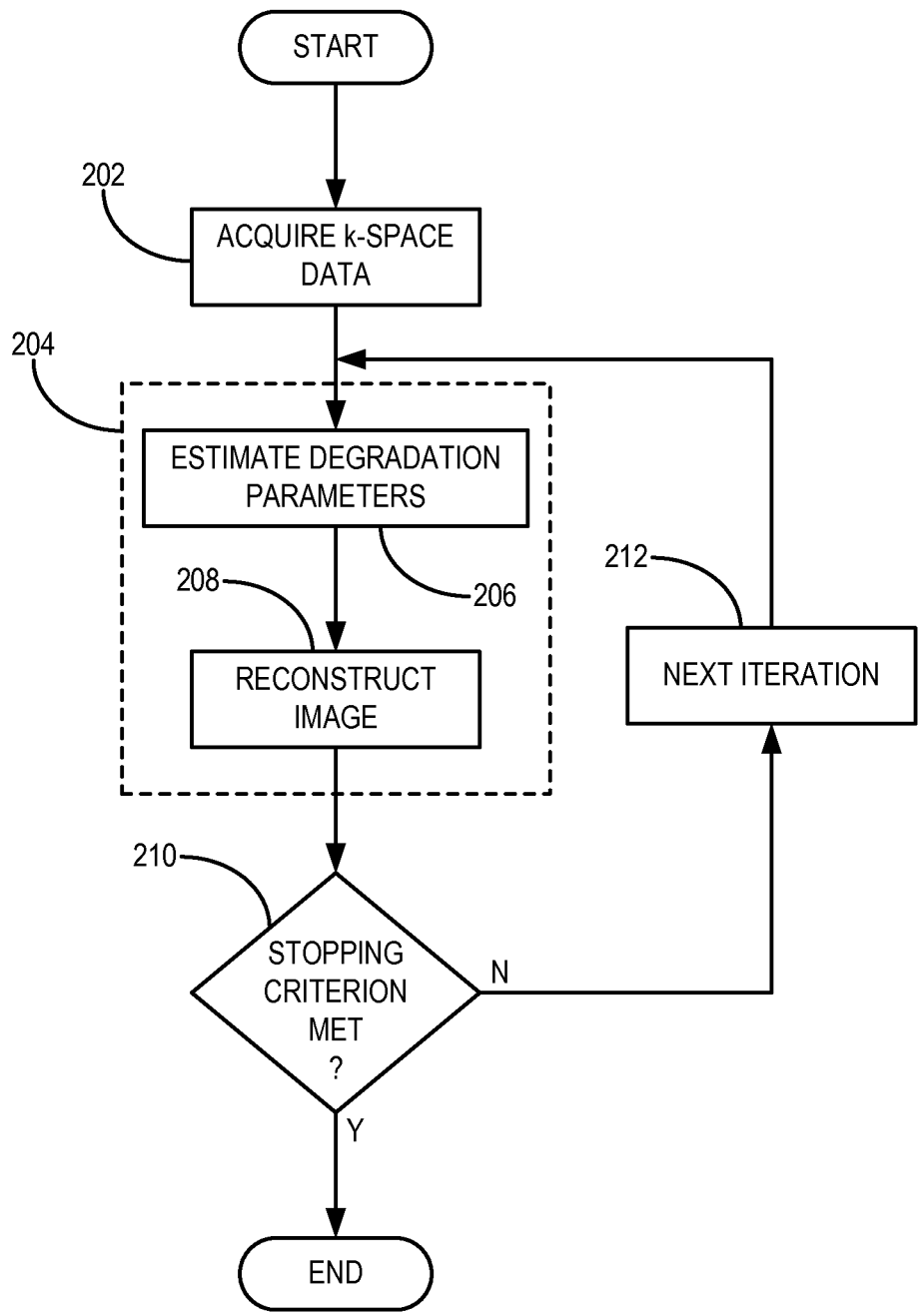
FIG. 2 is a flowchart setting forth the steps of an example of a method for jointly estimating image degradation parameters and reconstructing an image in which the image degradation associated with the estimated image degradation parameters is mitigated.

Referring now to FIG. 2, a flowchart setting forth the steps of a method for the joint estimation of degradation parameters and reconstruction of an image in which effects of that estimated degradation have been mitigated is illustrated. This method may be referred to as an "acquisition diversity for dynamic estimation and reconstruction" ("ADDER") method.

The MRI system is operated to acquire k-space data from the subject, as indicated at step 202. In particular, the k-space data that is acquired is representative of multiple different images of the subject. For instance, K different measurements, $m_k$, are made at different points in time, each given by the following:

$$m_k = fH_k(g) + w_k \tag{15}$$

where $H_k(g)$ represents the forward model matrix associated with the $k^{th}$ acquisition. The forward model matrix associated with the $k^{th}$ acquisition, $H_k(g)$, is related to the underlying forward model matrix, H, of Eqn. (12) by $$H_k(g) = T_k(H;g) \tag{16}$$

for k=1, ..., K, and where $T_k$ is a carefully chosen transformation with specific properties discussed below. Because K images are acquired rather than one, some considerations may have to be made in the data acquisition. For example, if the imaging time is to remain under a certain threshold, and if including the K−1 additional acquisitions exceeds that threshold, then certain trade-offs have to be made to reduce imaging time. These trade-offs could be chosen depending on the application of interest, and may include reducing the value of imaging parameters, such as image quality, SNR, or resolution in each measured image, $m_k$. This trade-off leads to a penalty term that can be included in each $H_k$ and is a function of K and $T_k$. On the other hand, if the inclusion of the K−1 additional acquisitions does not exceed the minimum time threshold, then no trade-offs need to be made in the data acquisition. This is advantageous, particularly in pulse sequences such as three-dimensional EPI, which is much faster than two-dimensional EPI, yet suffers from more severe degradations due to larger SIC values. Traditionally, three-dimensional EPI is avoided in the clinic because of its extreme sensitivity to degradations. Using the method of the present invention, however, three-dimensional EPI can be implemented in the clinic because the severe degradations are mitigated. Thus, the method of the present invention allows three-dimensional EPI to be used in the clinic without increases in scan time and without trade-offs such as those described above.

After the k-space data has been acquired, the underlying degradation is jointly estimated while reconstructing an image of the subject, as indicated generally at block 204. The first step of this joint estimation reconstruction process is the estimation of the underlying degradation, as indicated at step 206. For instance, using the K measurements, $\{m_1, \ldots, m_K\}$, the underlying SICs, g, may be estimated as the vector that best explains a measurement $m_j$, given $m_i$, for all indices, i. That is, the following minimization problem may be solved:

$$\hat{g} = \underset{g}{\operatorname{argmin}} \sum_{1 \leq j \leq K} \left\| \hat{f}(\tilde{m}; g) H_j(g) - m_j \right\|^2; \tag{17}$$

where $\tilde{m}$ is the concatenated K-channel measurement vector and $\hat{f}(\tilde{m};g)$ is an estimate of the object reconstructed from all the measurements $\tilde{m}$, assuming the actual SIC is given by g. The minimization in Eqn. (17) may be solved, for example, using an adaptive simulated annealing algorithm.

As indicated at step 206, the object estimate, $\hat{f}$, in Eqn. (17) is jointly reconstructed with the estimation of the degradation parameters. For instance, given an estimate of g, the set of K forward model matrices, $H_k$, may be computed and an estimate of the object, $\hat{f}$, may be reconstructed using a multichannel deconvolution formulation, $$\hat{f}(\tilde{m}; \hat{g}) = \operatorname{argmin} \left\| \tilde{m} - fH_{1:K}(\hat{g}) \right\| + \lambda J(f); \tag{18}$$

where $H_{1:K}$ is the concatenation of the K-channel forward model matrices, estimated assuming an SIC distribution, $\hat{g}$. In Eqn. (18), J(f) is a regularization term and λ is a regularization parameter. The minimization in Eqn. (18) may be solved using, for example, an implementation of the Landweber algorithm. The estimation reconstruction steps are iteratively repeated until a stopping criteria is reached, as indicated at decision block 210 and iteration step 212.

Equations (17) and (18) define a joint estimation reconstruction approach for computing SIC terms and recovering an image of the subject in which degradation caused by the SIC terms is substantially mitigated. The formulation presented in these equations uses an $l_2$-metric; however, it will be appreciated by those skilled in the art that other metrics could be readily adopted, including an $l_1$-norm in the estimation step, a probability of detection, or a classification performance in the reconstruction step. Equations (16)(18) are the foundation for a joint acquisition-reconstruction paradigm. These equations define a unifying framework that can be used to jointly optimize acquisition and processing parameters for minimizing inhomogeneity-induced susceptibility artifacts in EPI and other MRI pulse sequences and imaging applications.

The transformation, $T_k$, discussed above is selected to preferably satisfy the following properties. First, the set of matrices, $\{H_k\}$, should result in diverse measurement of the object, f. Intuitively, this can be motivated by the following observation. If all $H_k$ were similar, that is to say if they were minimally diverse, then the ability to discriminate the measurements becomes compromised and the estimation performed via Eqn. (17) becomes adversely affected. Second, the matrices, $\{H_k\}$, should yield measurements with a quality metric larger than the underlying noise level. Indeed, a non-careful choice of the matrices, $\{H_k\}$, may yield measurements that are dominated by noise, which would negatively affect the reconstruction performed via Eqn. (18). One example of the transformation, $T_k$, and a corresponding reconstruction algorithm are now provided.

An example of a multi-acquisition method associated with step 202 described above is now provided. It is desirous to acquire k-space data such that a transformation, $T_k$, that modulates the degradation to be estimated can be established. For example, a transformation, $T_k$, that modulates the SIC terms in Eqn. (12) so as to generate a diverse set of measurements may be desired. An example of such a transformation, $T_k$, is as follows:

$$T_k(H)_{(g)} = \exp\left(i2\pi\left(\frac{nq}{N_y}\right)\right)\exp(i2\pi\gamma g_0(x_p, y_q)(TE_k + nT)) \cdot \text{sinc}\left(\frac{n}{N_y}\right) \quad (19)$$

$$M_k \text{sinc}(\pi\gamma\Delta z(g_1(x_p, y_q)(TE_k + nT)) - g_{c_k}\tau_c);$$

where $M_k$ denotes a magnitude penalty term (if any), $TE_k$ denotes the value of the echo time for the $k^{th}$ acquisition, and $g_{c_k}$ is a compensation gradient introduced during the $k^{th}$ acquisition for a period of time, $\tau_c$. It should be noted that from the form of Eqn. (19), the set of compensation gradients $\{g_{c_k}\}$ can be used to shift the sin c term, thereby modulating the $g_1(x_p, y_q)$ term and $H_k$. This also has the effect of modulating the magnitude of the measurements, $m_k$. Similarly, the variable echo time, $TE_k$, can be used to modulate the $g_0(x_p, y_q)$ term, $H_k$, and the phase of $m_k$.

The pulse sequence that generates such a forward model matrix is essentially a variable echo time "z-shim" sequence, whereby a known gradient area is introduced along the z-direction during acquisition, each at a given echo time. This is repeated K times for each slice of interest. Associated with this multi-acquisition in two-dimensions is a tradeoff for acquiring K−1 additional measurements. In other words, the z-shim pulse sequence should be designed to keep the imaging time of the volume-of-interest constant. This can be achieved by reducing of the number of samples captured ("undersampling" of the FOV), increasing the scan bandwidth (if possible), reducing the number of imaged slices, and so on. By way of example, a z-shim protocol in which a reduced number of distinct slices per volume is acquired during the same repetition time ("TR") may be used.

It can be shown from Eqn. (20) below that the penalty term associated with the aforementioned trade-off is an exponential reduction in measurement SNR as a function of K. The reason for this decay is because the slice of interest is acquired (excited) K times during the same TR (i.e., partial saturation). By way of example, when the k-space data is acquired with a flip angle equal to the Ernst angle of gray matter, the magnitude of $H_k$ is reduced by a factor $M_k$, which may be given by, $$M_K = M_0 \sqrt{\frac{1 - \exp\left(-\frac{TR}{T1 \cdot K}\right)}{1 + \exp\left(-\frac{TR}{T1 \cdot K}\right)}}; \quad (20)$$

where $T_1$ is the relaxation constant of gray matter and $M_0$ is the maximum available magnetization. To satisfy the properties discussed above, the choice of the set of compensation gradients, $\{g_{c_k}\}$, and the set of echo times, $\{TE_k\}$, affects the performance of the MBER method. The choice of these parameters can therefore be optimized to achieve a desired reconstruction performance. By way of example, the set of compensation gradients, $\{g_{c_k}\}$, and the set of echo times, $\{TE_k\}$, can be selected to be uniformly spaced on a predefined range of interest. One particular example for a 3 Tesla ("T") main magnetic field strength includes echo times that are uniformly spaced between 20-30 milliseconds ("ms") with steps of 5 ms. This chosen step size results in the estimation of $g_0$ terms that are in the range of ±100 Hertz. Continuing with the example, the compensation gradients, $\{g_{c_k}\}$ may be chosen in the range±9 milliTesla-millisecond per meter mT·ms/m. Compensation gradients in this range correct for $g_1$ terms that are in the range of ±300 μT/m.

It is contemplated that the iterative inversion of the multi-channel matrix, $H_{1:K}$, is less susceptible to noise amplification. The reason for this is that K measurements are acquired, each of which are generated by a forward model matrix with a differently shifted sine, per Eqn. (19). Thus, a given region with large $g_1(x_p, y_q)$ is less likely to suffer from complete signal loss in all K measurements, as compared to methods that only acquire one measurement. This will overcome the need to implement complicated inversion method such as the one described by Liu and Ogawa discussed above.

It is again noted that the foregoing example of modifying an EPI pulse sequence to modulate shift-variant inhomogeneity coefficients is but one application of the method of the present invention. Other examples, with different diverse multi-acquisition strategies and corresponding tradeoff space, could be readily adopted by those skilled in the art.

Figure 3:
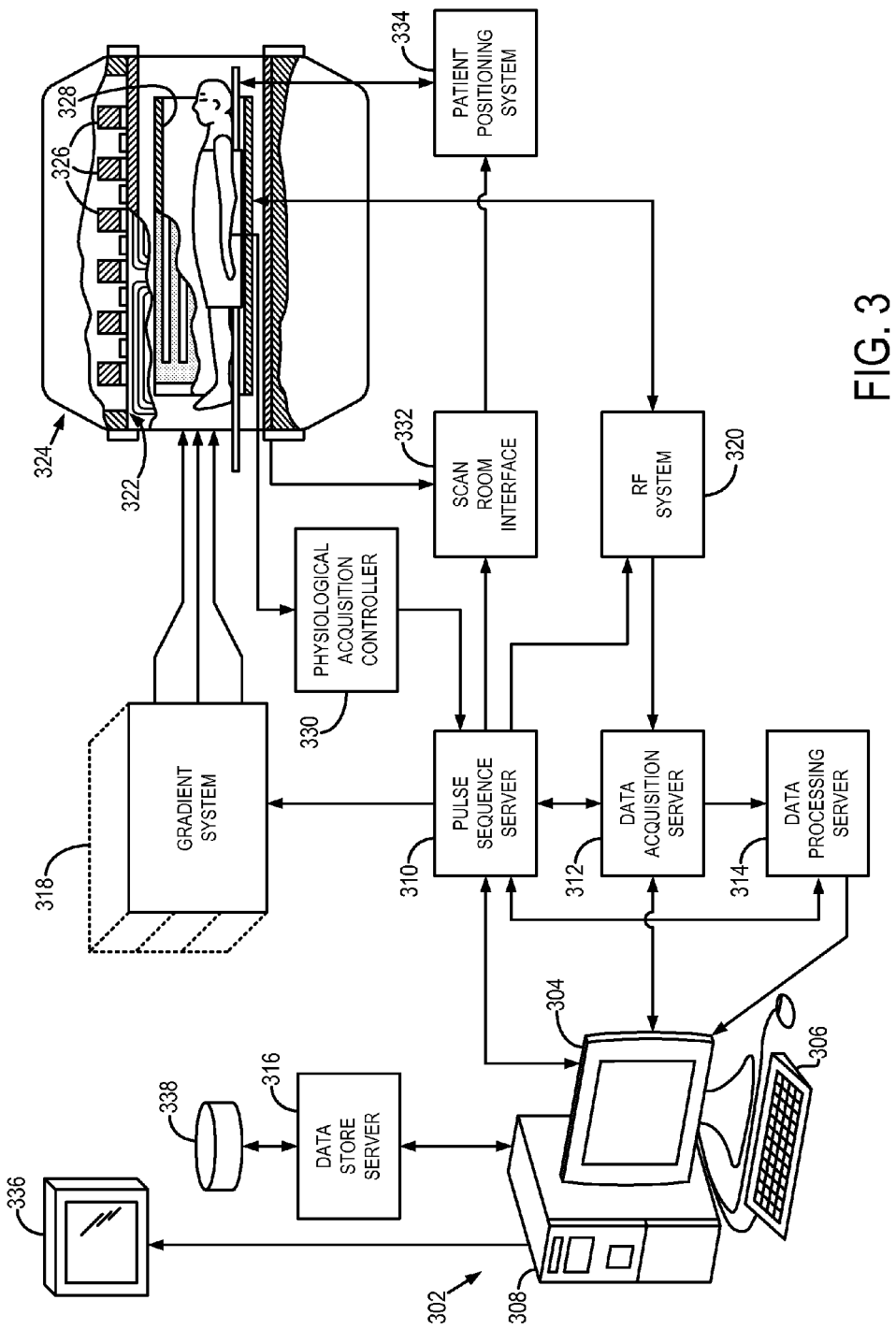
FIG. 3 is a block diagram of an example magnetic resonance imaging system.

Referring particularly now to FIG. 3, an example of a magnetic resonance imaging ("MRI") system 300 is illustrated. The MRI system 300 includes a workstation 302 having a display 304 and a keyboard 306. The workstation 302 includes a processor 308, such as a commercially available programmable machine running a commercially available operating system. The workstation 302 provides the operator interface that enables scan prescriptions to be entered into the MRI system 300. The workstation 302 is coupled to four servers: a pulse sequence server 310; a data acquisition server 312; a data processing server 314; and a data store server 316. The workstation 302 and each server 310, 312, 314, and 316 are connected to communicate with each other.

The pulse sequence server 310 functions in response to instructions downloaded from the workstation 302 to operate a gradient system 318 and a radiofrequency ("RF") system 320. Gradient waveforms necessary to perform the prescribed scan are produced and applied to the gradient system 318, which excites gradient coils in an assembly 322 to produce the magnetic field gradients $G_x$, $G_y$, and $G_z$ used for position encoding MR signals. The gradient coil assembly 322 forms part of a magnet assembly 324 that includes a polarizing magnet 326 and a whole-body RF coil 328.

RF excitation waveforms are applied to the RF coil 328, or a separate local coil (not shown in FIG. 3), by the RF system 320 to perform the prescribed magnetic resonance pulse sequence. Responsive MR signals detected by the RF coil 328, or a separate local coil (not shown in FIG. 3), are received by the RF system 320, amplified, demodulated, filtered, and digitized under direction of commands produced by the pulse sequence server 310. The RF system 320 includes an RF transmitter for producing a wide variety of RF pulses used in MR pulse sequences. The RF transmitter is responsive to the scan prescription and direction from the pulse sequence server 310 to produce RF pulses of the desired frequency, phase, and pulse amplitude waveform. The generated RF pulses may be applied to the whole body RF coil 328 or to one or more local coils or coil arrays (not shown in FIG. 3).

The RF system 320 also includes one or more RF receiver channels. Each RF receiver channel includes an RF amplifier that amplifies the MR signal received by the coil 328 to which it is connected, and a detector that detects and digitizes the I and Q quadrature components of the received MR signal. The magnitude of the received MR signal may thus be determined at any sampled point by the square root of the sum of the squares of the I and Q components:

$$M = \sqrt{I^2 + Q^2} \tag{21}$$

and the phase of the received MR signal may also be determined:

$$\varphi = \tan^{-1}\left(\frac{Q}{I}\right). \tag{22}$$

The pulse sequence server 310 also optionally receives patient data from a physiological acquisition controller 330. The controller 330 receives signals from a number of different sensors connected to the patient, such as electrocardiograph ("ECG") signals from electrodes, or respiratory signals from a bellows or other respiratory monitoring device. Such signals are typically used by the pulse sequence server 310 to synchronize, or "gate," the performance of the scan with the subject's heart beat or respiration.

The pulse sequence server 310 also connects to a scan room interface circuit 332 that receives signals from various sensors associated with the condition of the patient and the magnet system. It is also through the scan room interface circuit 332 that a patient positioning system 334 receives commands to move the patient to desired positions during the scan.

The digitized MR signal samples produced by the RF system 320 are received by the data acquisition server 312. The data acquisition server 312 operates in response to instructions downloaded from the workstation 302 to receive the real-time MR data and provide buffer storage, such that no data is lost by data overrun. In some scans, the data acquisition server 312 does little more than pass the acquired MR data to the data processor server 314. However, in scans that require information derived from acquired MR data to control the further performance of the scan, the data acquisition server 312 is programmed to produce such information and convey it to the pulse sequence server 310. For example, during prescans, MR data is acquired and used to calibrate the pulse sequence performed by the pulse sequence server 310. Also, navigator signals may be acquired during a scan and used to adjust the operating parameters of the RF system 320 or the gradient system 318, or to control the view order in which k-space is sampled. The data acquisition server 312 may also be employed to process MR signals used to detect the arrival of contrast agent in a magnetic resonance angiography ("MRA") scan. In all these examples, the data acquisition server 312 acquires MR data and processes it in real-time to produce information that is used to control the scan.

The data processing server 314 receives MR data from the data acquisition server 312 and processes it in accordance with instructions downloaded from the workstation 302. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 314 are conveyed back to the workstation 302 where they are stored. Real-time images are stored in a data base memory cache (not shown in FIG. 3), from which they may be output to operator display 312 or a display 336 that is located near the magnet assembly 324 for use by attending physicians. Batch mode images or selected real time images are stored in a host database on disc storage 338. When such images have been reconstructed and transferred to storage, the data processing server 314 notifies the data store server 316 on the workstation 302. The workstation 302 may be used by an operator to archive the images, produce films, or send the images via a network to other facilities.

Thus, a joint acquisition processing method for reconstructing magnetic resonance images that would otherwise be corrupted by degradations has been provided. As one example, a multi-acquisition method that acquires diverse, correlated views of the same imaging slice by applying K z-compensation gradients at K echo times has been provided. The method also includes a joint estimation reconstruction algorithm. The estimation step is capable of calculating the inherent image degradation, for example, by estimating shift-variant inhomogeneity coefficients that best explain the acquired data from an MMSE sense. The estimation step is a powerful tool that can also be used as a robust and dynamic field mapping routine. The method does not require any prior knowledge of the field maps. The reconstruction step uses the information computed by the estimation step, along with the acquired k-space data, to derive an MMSE estimate of the object. The reconstruction estimation steps are iteratively repeated until a stopping criteria is reached.

The method can also be used to dynamically extract physiological values from degradations using the acquired data. Other methods in the literature need to acquire such scans separately and have to assume that such parameters do not change over time. This is an incorrect assumption. Physiology changes over time, and its effects need to be measured from data dynamically without the need for a separate scan.

Even in cases of severe signal loss, the presented estimation reconstruction method is able to combine the diverse measurements and recover the signal in the affected regions. This is a major advantage over existing methods, which are limited by the inherent signal-to-noise ratio level across the image. As an example of a data acquisition strategy that acquires diverse measurements, a modified EPI pulse sequence was presented. Other modified pulse sequences and corresponding diverse acquisition strategies, albeit with different tradeoffs, can be readily implemented. Finally, it is noted that the method of the present invention allows the ability to jointly optimize the transformation, $T_k$, along with the reconstruction performance. In fact, one example would be to optimize the choice of the compensation gradients and echo times so as to maximize reconstruction performance.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for jointly estimating an image degradation and reconstructing an image of a subject using a magnetic resonance imaging (MRI) system, the steps of the method comprising:
   a) acquiring a k-space data set using the MRI system;
   b) repeating step a) to acquire multiple k-space data sets while using a different acquisition parameter during each repetition of step a) such that each of the multiple k-space data sets is acquired using a different acquisition parameter;
   c) jointly estimating the image degradation and reconstructing an image of the subject in which the image degradation is mitigated by iteratively performing the steps of:
      i) estimating the image degradation from the multiple k-space data sets acquired in steps a) and b); and
      ii) reconstructing the image of the subject in which the image degradation is mitigated using the image degradation estimated in step c)i) and the multiple k-space data sets acquired in steps a) and b).

2. The method as recited in claim 1 in which the different acquisition parameters are selected to modulate the acquired k-space data as a function of the image degradation to be estimated.

3. The method as recited in claim 1 in which step c)i) includes minimizing a difference between a forward projection of an estimate of the reconstructed image and the acquired k-space data, and in which the forward projection of the reconstructed image is computed using a forward model matrix that is a function of the image degradation.

4. The method as recited in claim 3 in which the forward model matrix modulates the image degradation so as to produce a diverse set of k-space measurements.

5. The method as recited in claim 3 in which step c)i) includes minimizing a norm of the difference between the forward projection of the estimate of the reconstructed image and the acquired k-space data.

6. The method as recited in claim 5 in which the norm is at least one of an $L_2$-norm and an $L_1$-norm.

7. The method as recited in claim 1 in which the image degradation estimated in step c)i) is caused by magnetic field inhomogeneities and the image degradation is estimated by estimating shift-variant inhomogeneity coefficients.

8. The method as recited in claim 1 in which step c)ii) includes minimizing a difference between the acquired k-space data and a forward projection of the reconstructed image, and in which the forward projection of the reconstructed image is computed using a forward model matrix that is a function of the image degradation estimated in step c)i).

9. The method as recited in claim 8 in which step c)ii) includes minimizing a norm of the difference between the acquired k-space data and the forward projection of the reconstructed image.

10. The method as recited in claim 9 in which the norm is at least one of an $L_2$-norm and an $L_1$-norm.

11. The method as recited in claim 1 in which the k-space data sets acquired in steps a) and b) are each acquired using a pulse sequence that includes a compensation gradient that modulates the image degradation, and in which the different acquisition parameter is a different amplitude of the compensation gradient.

12. The method as recited in claim 1 in which the k-space data sets acquired in steps a) and b) are each acquired at a different echo time in order to modulate the image degradation.

* * * * *